US00PP34982P3

(12) United States Plant Patent
Perrault et al.

(10) Patent No.: US PP34,982 P3
(45) Date of Patent: Feb. 14, 2023

(54) HOP PLANT NAMED 'HBC 843'

(50) Latin Name: *Humulus lupulus*
Varietal Denomination: HBC 843

(71) Applicant: HOP BREEDING COMPANY, L.L.C., Yakima, WA (US)

(72) Inventors: Jason Perrault, Toppenish, WA (US); Eugene G. Probasco, Yakima, WA (US); Michael D. Ferguson, Yakima, WA (US); Scott Varnum, Ellensburg, WA (US); Jaime Avalos P., Granger, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 17/300,968

(22) Filed: Dec. 30, 2021

(65) Prior Publication Data

US 2022/0217884 P1 Jul. 7, 2022

Related U.S. Application Data

(60) Provisional application No. 63/205,708, filed on Dec. 30, 2020.

(51) Int. Cl.
*A01H 5/02* (2018.01)
*A01H 6/00* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
CPC ..... A01H 5/02; A01H 5/08
See application file for complete search history.

*Primary Examiner* — Kent L Bell
(74) *Attorney, Agent, or Firm* — Svendsen Legal, LLC

(57) ABSTRACT

A new hop plant named 'HBC 843' is disclosed. 'HBC 843' is used for its exceptional and unique aromatic qualities, and is suitable for beer flavoring.

5 Drawing Sheets

Genus and species: *Humulus lupulus*.
Variety denomination: 'HBC 843'.

STATEMENT REGARDING FEDERALLY SPONSORED RESEARCH OR DEVELOPMENT

None

BACKGROUND OF THE INVENTION

'HBC 843' is a product of a controlled breeding program carried out by the inventors in the Yakima Valley of Washington State. 'HBC 843' was one of several seedlings resulting from a controlled cross made in 2012 with female parent '21055T', an unpatented variety, and male parent '83-95', also an unpatented variety. Seedling plants from this cross were planted in 2013 and screened for disease resistance and sex in a greenhouse and field nursery near Granger, Wash. A single plant of 'HBC 843' was selected in 2016. In 2016, 'HBC 843' was asexually reproduced via softwood cuttings, and expanded to 30 (thirty) plants in an evaluation block near Toppenish, Wash. In 2019, 'HBC 843' was further expanded to a one (1) acre test block near Moxee, Wash., with plants asexually reproduced via softwood cuttings produced from the evaluation block near Toppenish, Wash. The 'HBC 843' plants have now been observed and evaluated for several years. Throughout several generations of asexual propagation, 'HBC 843' has been observed to retain its distinctive characteristics and remain true to type.

SUMMARY OF THE INVENTION

A new and distinct hop plant is described herein, with the 'HBC 843' cultivar characterized by having cones with a high alpha acid content. The new cultivar exhibits cedar, lemon, honey, mango, orange, and rose aromas. The new cultivar is suitable for beer flavoring.

COMPARISON OF 'HBC 843' TO PARENT PLANTS AND COMPARISON CULTIVAR

'HBC 843' is distinguishable from its male parent '83-95' with flowers that develop into mature hop cones without producing pollen, while flowers of '83-95' produce pollen without developing into mature hop cones.

Table 1. below, sets forth some of the distinguishing characteristics of 'HBC 843' as compared to its female parent '21055T', and to 'Chinook', an unpatented variety, as a closely comparable cultivar.

TABLE 1

| | INSTANT CV. 'HBC 843' | FEMALE PARENT '21055T' | COMPARISON CV. 'CHINOOK' |
|---|---|---|---|
| Alpha (% of cone weight) | 14.0-15.0 | 14.7 | 11.5-15 |
| Beta (% of cone weight) | 4.5 | 5.7 | 3.0-4.0 |
| Co-humulone (% of alpha acids) | 27.5 | 42-45 | 27-31 |
| Total Oil (mL/100 g) | 1.2 | 2.0 | 1.0-2.5 |

BRIEF DESCRIPTION OF THE PHOTOGRAPHS

The 'HBC 843' hop plant is illustrated in the accompanying photographs, which show the plant's overall plant shape, leaf shape and cone shape plants nearing maturity at approximately four months of growth from the perennial rhizome.

Figure 1:
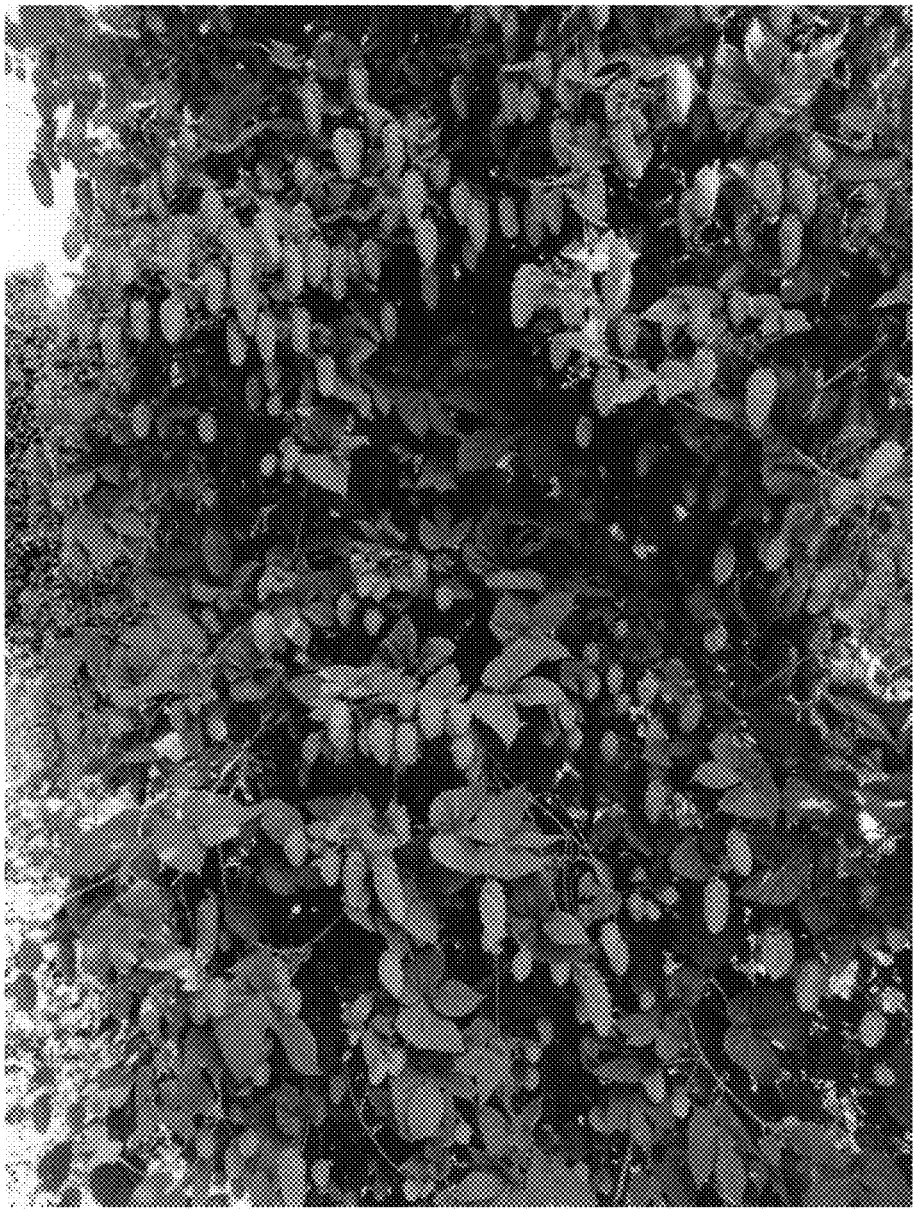
FIG. 1 illustrates a maturing 'HBC 843' hop plant as growing on a trellis.
Figure 2:
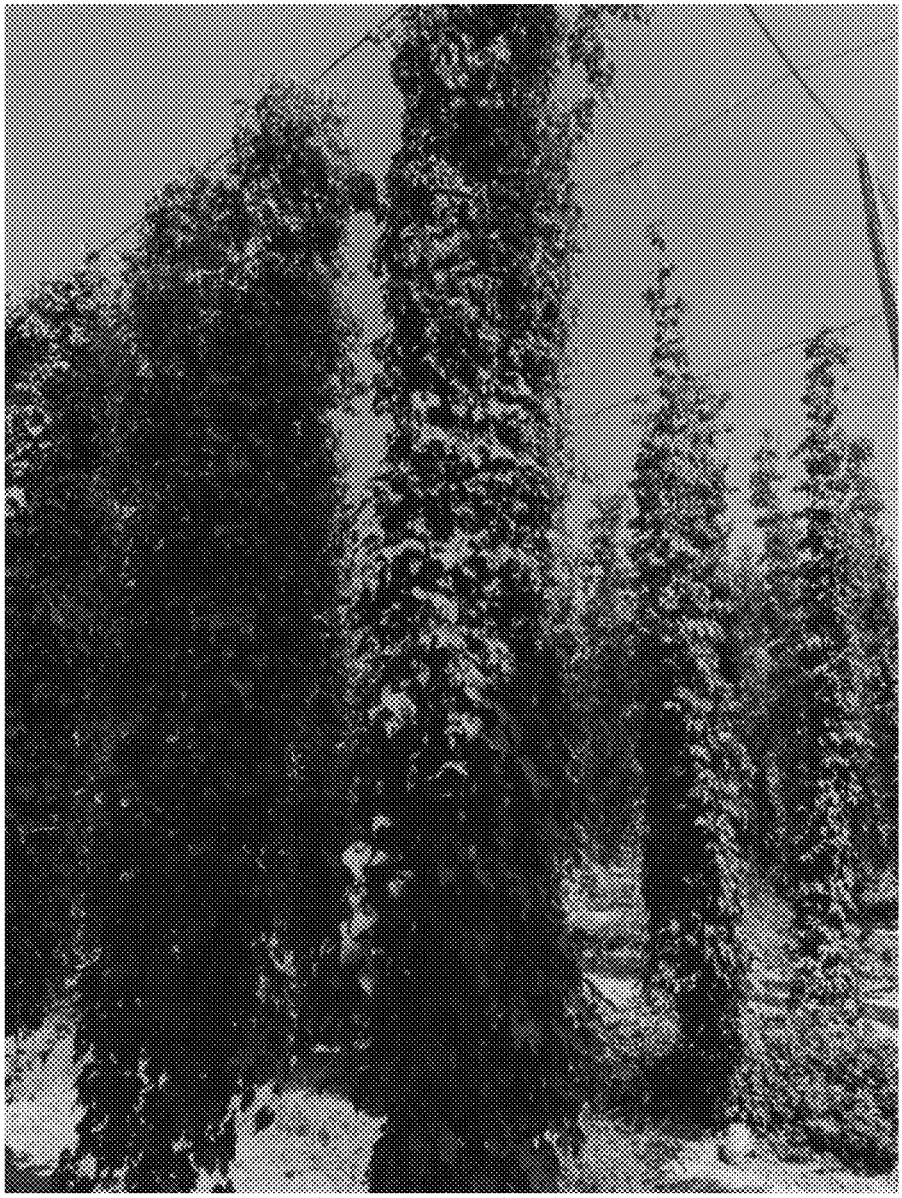
FIG. 2 illustrates a multiple of trellis with maturing 'HBC 843' hop plants.
Figure 3:
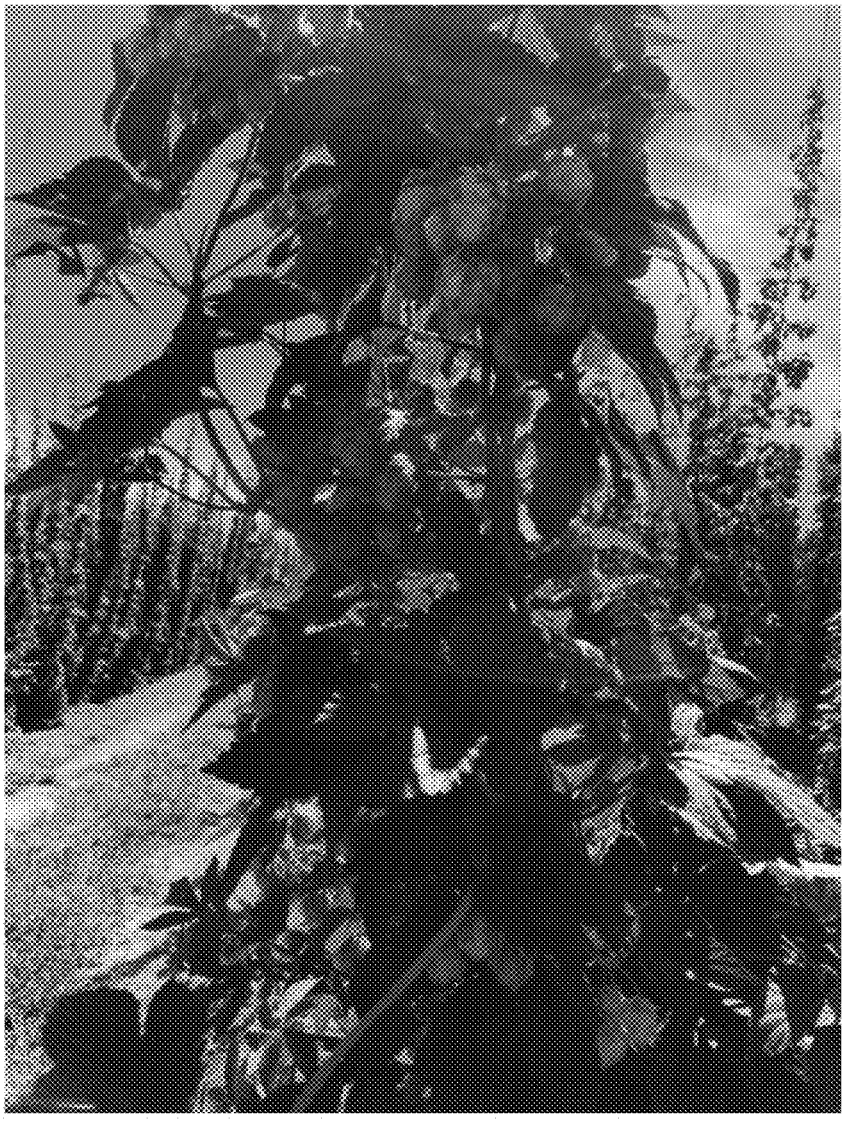
FIG. 3 illustrates bines of a mature 'HBC 843' hop plant as grown on a trellis.
Figure 4:
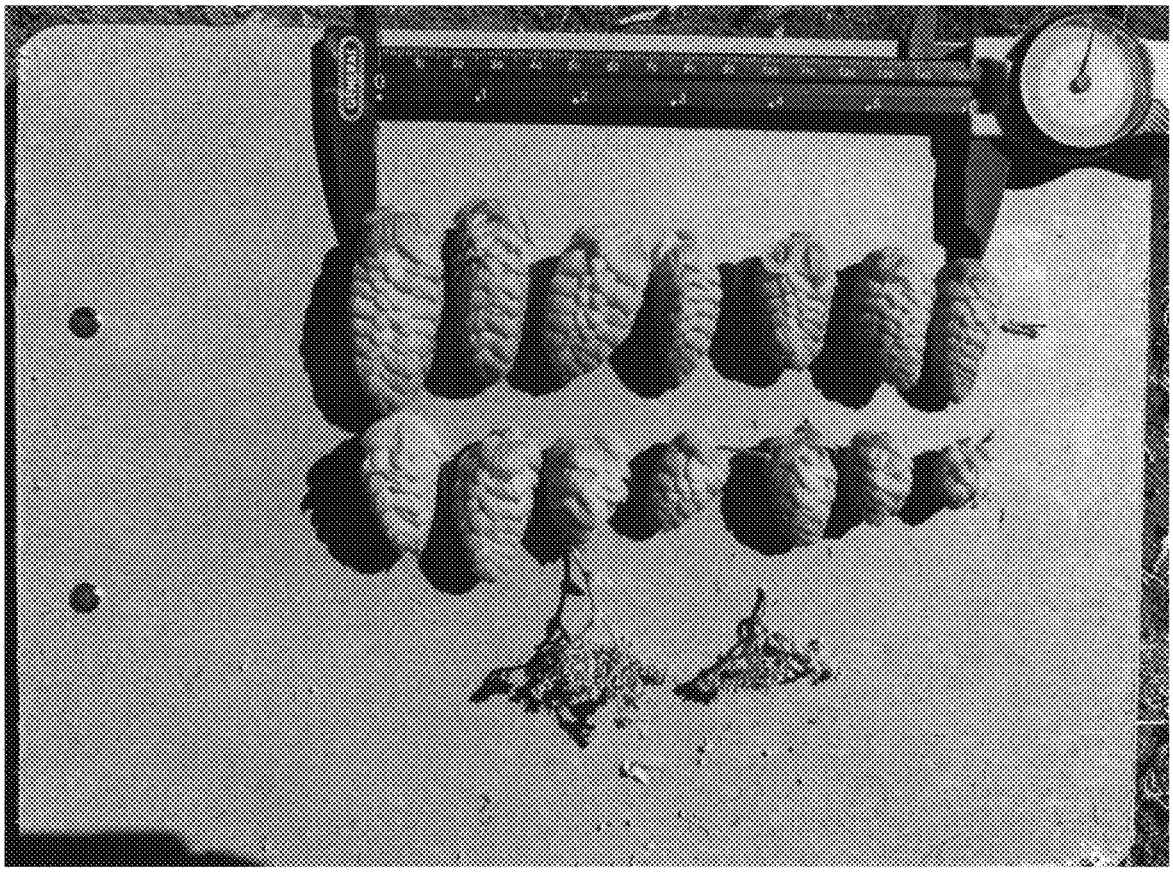
FIG. 4 illustrates whole mature cones and two male inflorescences (presumed sterile) of a 'HBC 843' hop plant.
Figure 5:
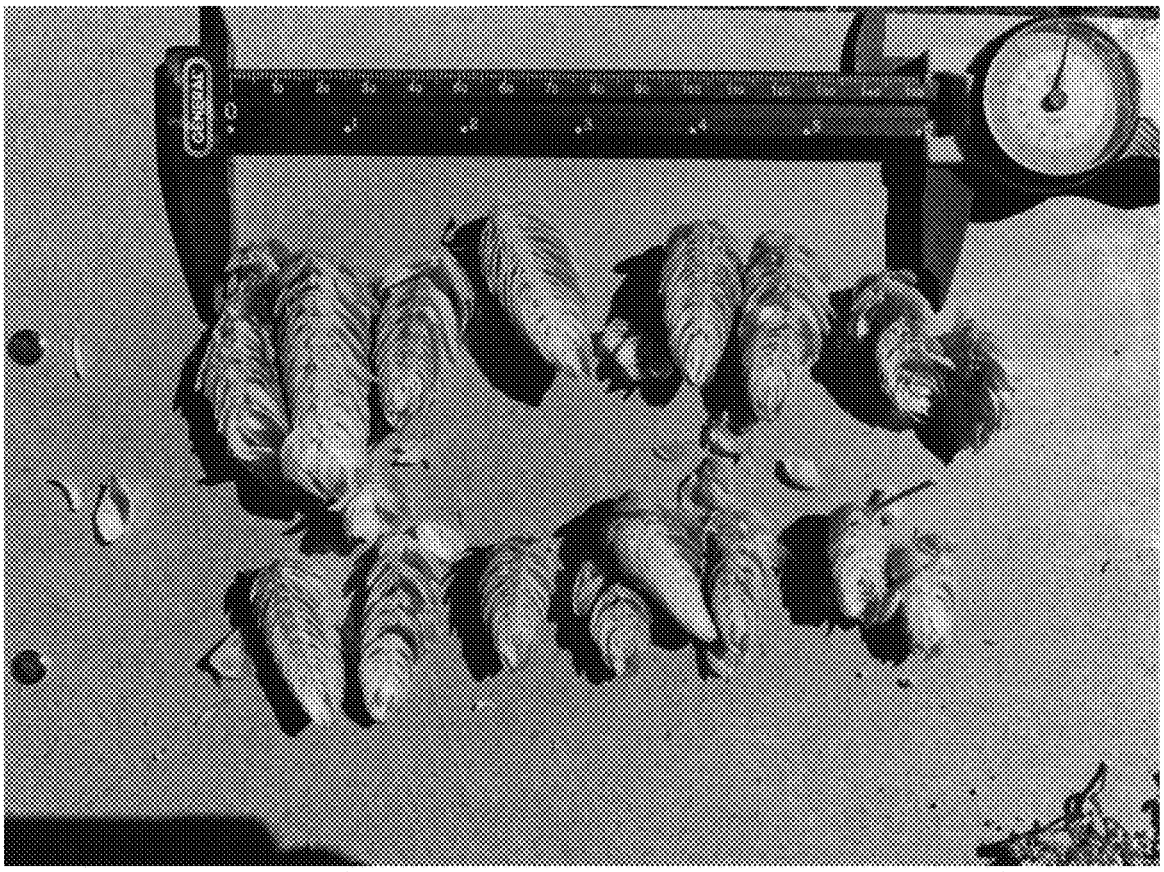
FIG. 5 illustrates cross sections of mature cones of a 'HBC 843' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made in the 2020 growing season, of plants nearing maturity plant at approximately four months of growth from the perennial rhizome, at the test block near Moxee, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Triploid.

Sex: Female.

Use: Brewing beer and ale.

Plant shape: Climbing bine, columnar growth, on typically 17 ft to 18 ft trellis height.

Yield: Average yield is expected to be approx. 2,500 to 2,700 pounds per acre.

Observed disease/pest resistance/susceptibility: Resistant to powdery mildew.

Harvest date: Typically harvested September 18 to September 25, but can deviate from this time period, depending on growing practices and location.

TABLE 2

| Oil Analytical Characteristics (Averages) | |
|---|---|
| % Alpha Acid (% cone weight) | 14 to 15 |
| % Beta Acid (% cone weight) | 4.5 |
| % Cohumulone (% alpha acids) | 27.5 |
| % Humulene (% of total oils) | 11 |
| % Caryphyllene (% of total oils) | 6.1 |
| % Farnesene (% of total oils) | 0.47 |
| % Linalool (% of total oils) | 0.24 |
| Total Oils (ml/100 g of cones): | 1.2 |
| Hop Storage Index (% loss) | 25 |
| Aroma Profile | Cedar, lemon, honey, mango, orange, rose. |

Hardiness: Observed Plant Hardiness Zone 6.

Freeze tolerance: Typically intolerant of freezing temperatures during the growing season.

Bine:

*Bine color*.—Yellow-Green 149D.
*Stripe present*.—Yes.
*Stripe color*.—Red-Purple 59B.
*Stipule direction*.—Up and Down.
*Stipule color*.—Yellow-Green 146B.
*Average number of stipules per bine*.—477.
*Bine diameter*.—15 mm at base; 10 mm at nine feet; and 5 mm at terminal end of eighteen feet.
*Typical bine length*.—6 m to 7 m.
*Typical internode length* (*bine*).—17.8 cm.
*Typical internode length* (*lateral*).—7.0 cm.
*Average lateral length* (*on bottom third of plant*).—56 cm.
*Average lateral length* (*on middle third of plant*).—128 cm.
*Average laterals length* (*on upper third of plant*).—56 cm.
*Lateral density* (*on middle third of plant*).—Medium (two laterals per node).

Leaf:

*Arrangement*.—Alternate to Opposite.
*Shape*.—Palmate.
*Apex*.—Aristulate.
*Base*.—Sagittate.
*Average length of mature leaf*.—18 cm.
*Average width of mature leaf*.—19 cm.
*Color of mature Leaf upper surface*.—Yellow-Green 147A.
*Color of mature Leaf lower surface*.—Yellow-Green 147B.
*Color of immature Leaf upper surface*.—Yellow-Green 144A.
*Color of immature Leaf lower surface*.—Green 138B.
*Number of lobes*.—1 to 7.
*Margin*.—Serrate.
*Serrations per inch*.—4 to 6 (typically).
*Pose*.—Down.
*Average petiole length* (*of mature leaf*).—12.1 cm.
*Average petiole diameter* (*of mature leaf*).—4.7 mm.
*Petiole color at base*.—Yellow-Green 145B.
*Venation*.—Palmate.
*Vein color*.—Yellow-Green 144C.

Cone:

*Avg. length*.—4 cm.
*Avg. diameter*.—22 mm.
*Cone shape*.—Oblong to Ovate.
*Bract tip color*.—Greyed-Yellow 162D.
*Bract base color*.—Yellow-Green 154C.
*Bract shape*.—Orbicular.
*Bract length*.—17.3 mm.
*Bract apex length*.—1.3 mm.
*Bract width*.—15.7 mm.
*Bract tip shape*.—Cuspidate.
*Bract tip position*.—Recurved Downward.
*Bract base shape*.—Rounded.
*Bract margin*.—Entire.
*Degree of bract opening* (*closed, slightly open, clearly open*).—Very slightly open.
*Bracteole color* (*lower surface*).—Yellow-Green 149C.
*Bracteole color* (*upper surface*).—Yellow-Green 145B.
*Bracteole shape*.—Ovate.
*Bracteole length*.—13 mm.

*Bracteole width.*—7.3 mm.

*Lupulin glands shape.*—Peduncutlated oblong polyps.

*Lupulin glands number per cone.*—Varies greatly — Moderate to many.

*Lupulin glands color.*—Yellow-Green 6A.

*Time of flowering.*—Mid to late July.

*Maturity date range* (*early, medium, late*).—Late.

What is claimed:

1. A new and distinct variety of Hop plant named 'HBC 843', substantially as illustrated and described herein.

* * * * *